United States Patent [19]

Bradshaw et al.

[11] Patent Number: 4,777,179
[45] Date of Patent: Oct. 11, 1988

[54] HETEROCYCLIC DERIVATIVES, PROCESSES FOR THE USE THEREOF AND PHARMACEUTICAL COMPOSITIONS CONTAINING THEM

[75] Inventors: John Bradshaw; Duncan B. Judd, both of Ware; Barry J. Price, Hertford; John W. Clitherow, Sawbridgeworth; John W. M. Mackinnon; Linda Carey, both of Royston; Roger Hayes, Potters Bar, all of Great Britain

[73] Assignee: Glaxo Group Limited, London, England

[21] Appl. No.: 789,578

[22] Filed: Oct. 21, 1985

Related U.S. Application Data

[63] Continuation of Ser. No. 429,135, Sep. 30, 1982, abandoned, which is a continuation of Ser. No. 199,720, Oct. 23, 1980, abandoned.

[30] Foreign Application Priority Data

Oct. 23, 1979 [GB] United Kingdom ............... 7936762
Jun. 5, 1980 [GB] United Kingdom ............... 8018404

[51] Int. Cl.$^4$ ................ A61K 31/445; A61K 31/41; C07D 403/12; C07D 403/14; C07D 249/14; C07D 401/10; C07D 413/10
[52] U.S. Cl. ................... 514/383; 514/188; 514/212; 514/326; 514/340; 514/363; 514/227.8; 514/236.2; 540/480; 540/481; 540/597; 540/598; 540/602; 540/603; 544/60; 544/124; 544/131; 544/133; 546/193; 546/209; 546/210; 546/267; 548/266; 548/267
[58] Field of Search ............ 544/60, 130, 124, 131, 544/132, 133; 549/129; 540/480, 481, 597, 598, 602, 603; 546/208, 210, 193, 209, 267; 548/266, 267; 514/188, 212, 222, 230, 326, 340, 363, 383, 283

[56] References Cited

U.S. PATENT DOCUMENTS 4,318,913  3/1982  Clitherow et al. ............ 548/267
4,323,566  4/1982  Clitherow et al. ............ 548/267
4,536,508  8/1985  Clitherow et al. ............ 548/267

Primary Examiner—Robert T. Bond
Attorney, Agent, or Firm—Bacon & Thomas

[57] ABSTRACT

The invention provides compounds of the general formula

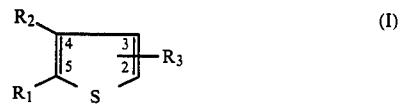

and physiologically acceptable salts and hydrates thereof, in which one of $R_1$ and $R_2$ represents hydrogen, halogen or a $C_{1-4}$ alkyl group which may be optionally substituted by hydroxy or $C_{1-4}$ alkoxy, and the other represents the group $R_4R_5NAlk-$ in which Alk represents a straight or branched alkylene chain of 1 to 6 carbon atoms;

$R_3$, which may be in either the 2 or 3-position, represents the

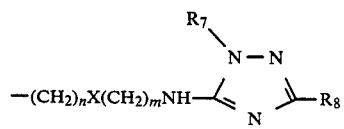

where X represents $-CH_2-$, $-O-$ or $-S-$;
n represents zero, 1 or 2;
m represents 2, 3 or 4; and
$R_7$ represents hydrogen, alkyl, alkenyl, aralkyl, or $C_{2-6}$ alkyl substituted by hydroxy or alkoxy; and
$R_8$ represents hydrogen, alkyl, alkenyl, aralkyl, hydroxyalkyl, acyloxyalkyl, alkoxyalkyl, aryloxyalkyl, aralkyloxyalkyl, aminoalkyl, alkylaminoalkyl, dialkylaminoalkyl, hydroxy or alkoxy, or the group $NR_{10}R_{11}$; with the provisos that
where $R_2$ represents the group $R_4R_5NAlk$ then $R_3$ is in the 2-position;
where $R_2$ represents hydrogen then $R_3$ is in the 3-position; and
where $R_2$ represents halogen or $C_{1-4}$ alkyl optionally substituted by hydroxy or $C_{1-4}$ alkoxy, and $R_3$ is in the 2-position, then $R_8$ cannot represent amino $C_{1-6}$ alkyl, $C_{1-6}$ alkylamino $C_{1-6}$ alkyl, di-$C_{1-6}$ alkylamino $C_{1-6}$ alkyl or a group $NR_{10}R_{11}$.

The compounds of formula (I) show pharmacological activity as selective histamine $H_2$-antagonists.

12 Claims, No Drawings

HETEROCYCLIC DERIVATIVES, PROCESSES FOR THE USE THEREOF AND PHARMACEUTICAL COMPOSITIONS CONTAINING THEM

This application is a continuation of application Ser. No. 429,135 filed Sept. 30, 1982, which is a continuation of application Ser. No. 199,720 filed Oct. 23, 1980, both now abandoned.

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol, Chemother 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236 385. Furthermore the compounds antagonise the effect of histamine on the contraction frequency of isolated guinea pig right atrium but do not modify histamine induced contractions of isolated gastro-intestinal smooth muscle which are mediated via $H_1$-receptors.

Compounds with histamine $H_2$-blocking activity may be used in the treatment of conditions where there is an advantage in lowering gastric acidity, particularly in gastric and peptic ulceration, as a propylactic measure in surgical procedures, and in the treatment of allergic and inflammatory conditions where histamine is a known mediator. Thus they may be used for example, either alone, or in combination with other active ingredients in the treatment of allergic and inflammatory conditions of the skin.

The present invention provides compounds of the general formula (I)

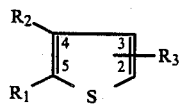

and physiologically acceptable salts, hydrates and bioprecursors thereof, in which one of $R_1$ and $R_2$ represents hydrogen, halogen or a $C_{1-4}$ alkyl group which may be optionally substituted by hydroxy or $C_{1-4}$ alkoxy, and the other represents the group $R_4R_5NAlk$— in which $R_4$ represents hydrogen, $C_{1-10}$ alkyl, cycloalkyl, alkenyl, alkynyl, aralkyl, heteroaralkyl, trifluoroalkyl, or alkyl substituted by hydroxy, alkoxy, amino, alkylamino, dialkylamino or cycloalkyl, and $R_5$ represents hydrogen or a $C_{1-4}$ alkyl group, or $R_4$ and $R_5$ may, together with the nitrogen atom to which they are attached, form a 5 to 10 membered ring which may be saturated or may contain at least one double bond, may be unsubstituted or may be substituted by one or more $C_{1-3}$ alkyl groups e.g. methyl, or a hydroxy group and/or may contain another heteroatom, e.g. oxygen or sulphur;

Alk represents a straight or branched alkylene chain of 1 to 6 carbon atoms, preferably 1 to 4 carbon atoms;

$R_3$, which may be in either the 2- or 3-position, represents the group

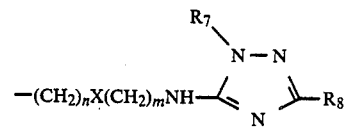

where X represents —$CH_2$—, —O— or —S—;
n represents zero, 1 or 2;
m represents 2, 3 or 4;

$R_7$ represents hydrogen, alkyl, alkenyl, aralkyl or $C_{2-6}$ alkyl substituted by hydroxy or alkoxy; and $R_8$ represents hydrogen, alkyl, alkenyl, aralkyl, hydroxyalkyl, acyloxyalkyl, alkoxyalkyl, aryloxyalkyl, aralkyloxyalkyl, aminoalkyl, alkylaminoalkyl, dialkylaminoalkyl, hydroxy or alkoxy, or the group $NR_{10}R_{11}$ where $R_{10}$ represents hydrogen, alkyl, alkyl substituted by hydroxy or $C_{1-3}$ alkoxy, alkenyl, aralkyl or heteroaralkyl, and $R_{11}$ represents any of the groups defined for $R_{10}$ or may represent $COR_{12}$ where $R_{12}$ represents hydrogen, alkyl, aryl, aralkyl, alkoxy, heteroaryl or heteroaralkyl, or $R_{11}$ represents the group $SO_2R_{13}$ where $R_{13}$ represents alkyl or aryl, or $R_{11}$ represents the group

where E represents oxygen or sulphur, and $R_{14}$ represents hydrogen, alkyl, cycloalkyl, aryl or aralkyl, or $R_{10}$ and $R_{11}$ taken together represent the group $=CR_{15}R_{16}$ where $R_{15}$ represents aryl or heteroaryl and $R_{16}$ represents hydrogen or alkyl, with the provisos that where $R_2$ represents the group $R_4R_5NAlk$ then $R_3$ is in the 2-position; and where $R_2$ represents hydrogen then $R_3$ is in the 3-position.

The term "alkyl" as a group or part of a group means that the group is straight or branched and has unless otherwise stated 1 to 6 carbo atoms, and in particular 1 to 4 carbon atoms e.g. methyl or ethyl and the terms "alkenyl" and "alkynyl" mean that the group has 3 to 6 carbon atoms. The term "cycloalkyl" means that the group has 3 to 8 carbon atoms. The term "aryl" as a group or part of a group preferably means phenyl or substituted phenyl, for example phenyl substituted with one or more $C_{1-3}$ alkyl or $C_{1-3}$ alkoxy groups or halogen atoms e.g. fluorine. The acyl portion of an acyloxyalkyl group means an aroyl, aralkanoyl or $C_{1-6}$ alkanoyl group. Examples of acyloxyalkyl groups include acetoxymethyl, formyloxymethyl, benzoyloxymethyl and phenylacetoxymethyl. The term "heteroaryl" as a group or part of a group within the definition of $R_4$ or $R_8$ means a 5 or 6 membered monocyclic unsaturated ring which may contain one or more heteroatoms selected from oxygen, nitrogen, and sulphur, e.g. furyl, pyridyl, thiazolyl or thienyl. The heteroaryl ring may be unsubstituted or substituted by $C_{1-3}$ alkyl, $C_{1-3}$ alkoxy, hydroxy, aminoalkyl, alkylaminoalkyl, dialkylaminoalkyl or halogen. The alkyl portion of a heteroaralkyl group is a straight or branched $C_{1-4}$ alkyl chain, and the heteroaryl ring is linked to the alkyl portion through either a carbon or nitrogen atom.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, tartrates, citrates, benzoates and fumarates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers. The term bioprecursors as used herein means compounds which have a structure different to that of the compounds of formula (I) but which, upon administration to an animal or human being, are converted in the body into a compound of formula (I).

The compounds according to the invention preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, e.g. $H_1$ antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 2 to 4 doses to the total of some 5 mg. to 2 g per day, preferably 5 to 500 mg. per day, dependent upon the condition of the patient.

Examples of suitable meanings for the groups $R_1$, $R_2$, $R_4$, $R_5$, $R_7$ and $R_8$ are as follows:

$R_1$ or $R_2$ (when other than the group $R_4R_5NAlk$): bromine atom or a $C_{1-3}$ alkyl group (e.g. methyl, ethyl or isopropyl) or a $C_{1-3}$ alkoxy $C_{1-3}$ alkyl group (e.g. methoxymethyl) or a hydroxy $C_{1-3}$ alkyl group (e.g. hydroxymethyl); or, when $R_1$ or $R_2$ is the group $R_4R_5NAlk$, $R_4$: alkyl (e.g. methyl, ethyl, propyl, butyl, pentyl, hexyl, heptyl or decyl), $C_{5-7}$ cycloalkyl (e.g. cyclopentyl, cyclohexyl or cycloheptyl), alkenyl (e.g. allyl or 3,3-dimethylallyl), aralkyl (e.g. phenylalkyl such as benzyl or phenethyl), $C_{1-4}$ alkyl substituted by a trifluoromethyl group (e.g. 2,2,2-trifluoroethyl), hydroxy $C_{2-4}$ alkyl (e.g. 3-hydroxypropyl), $C_{1-3}$ alkoxy $C_{2-4}$ alkyl (e.g. methoxyethyl or ethoxyethyl), di-$C_{1-3}$ alkylaminoalkyl (e.g. dimethylaminoethyl, diethylaminoethyl or dimethylaminopropyl) or heteroaralkyl where the heterocyclic portion represents for example a furyl, thienyl, pyrrolyl, pyridinyl, pyrimidinyl, triazinyl, oxazolyl, triazolyl or thiazolyl ring and the alkylene portion is for example a methylene, ethylene or propylene grouping; and $R_5$: hydrogen or a methyl or ethyl group; or $R_4R_5N$ may represent a 5–8 membered ring optionally containing one double bond and/or substituted by one or two $C_{1-3}$ alkyl (e.g. methyl) groups or a hydroxy group and/or containing an oxygen or sulphur atom (e.g. pyrrolidino, piperidino, hexamethylenimino, heptamethylenimino, tetrahydropyridino, 4-hydroxypiperidino, 4-$C_{1-3}$ alkylpiperidino (e.g. 4-methylpiperidino), morpholino, 2,6-di-$C_{1-3}$ alkylmorpholino (e.g. 2,6-dimethylmorpholino), or thiamorpholino);

$R_7$: hydrogen, $C_{1-4}$ alkyl (e.g. methyl, ethyl or propyl), or hydroxy-$C_{2-4}$ alkyl (e.g. 2-hydroxyethyl);

$R_8$: hydrogen, hydroxy, $C_{1-4}$ alkyl (e.g. methyl, ethyl or isobutyl), hydroxy $C_{1-4}$ alkyl (e.g. hydroxymethyl, 2-hydroxyethyl or 1-hydroxy-1-methylethyl), $C_{1-3}$ alkoxy $C_{1-4}$ alkyl (e.g. methoxymethyl or methoxyethyl), phenyl $C_{1-3}$ alkyl (e.g. benzyl or phenethyl), $C_{2-4}$ alkanoyloxy $C_{1-4}$ alkyl (e.g. acetoxymethyl), amino $C_{1-4}$ alkyl (e.g. aminomethyl), amino, $C_{1-4}$ alkylamino (e.g. methylamino or ethylamino) or di-$C_{1-4}$ alkylamino (e.g. dimethylamino, diethylamino or dipropylamino), phenyl $C_{1-3}$ alkylamino (e.g. benzylamino), or a heteroaryl $C_{1-3}$ alkylamino group where the heteroaryl ring is 5 or 6 membered and contains one heteroatom (e.g. 3- or 4-pyridylmethyl); or the group $NHCOR_{12}$ where $R_{12}$ represents hydrogen, $C_{1-3}$ alkyl (e.g. methyl or ethyl), $C_{1-3}$ alkoxy (e.g. methoxy or ethoxy), furyl, pyridyl, thiazolyl, thienyl, or phenyl optionally substituted by a $C_{1-3}$ alkyl (e.g. methyl) or $C_{1-3}$ alkoxy (e.g. methoxy) group; or the group $NHSO_2R_{13}$ where $R_{13}$ represents $C_{1-3}$ alkyl (e.g. methyl), or phenyl optionally substituted by a $C_{1-3}$ alkyl (e.g. methyl) or $C_{1-3}$ alkoxy (e.g. methoxy) group; or the group $NHCONHR_{14}$ where $R_{14}$ is $C_{1-3}$ alkyl (e.g. methyl), $C_{5-7}$ cycloalkyl (e.g. cyclohexyl), or phenyl optionally substituted by a $C_{1-3}$ alkyl (e.g. methyl) or $C_{1-3}$ alkoxy (e.g. methoxy) group; or the group $N=CHR_{15}$ where $R_{15}$ is a phenyl or pyridyl (e.g. 3- or 4-pyridyl) group.

The group Alk may be for example the group $(CH_2)_p$ where p is 1, 2 or 3.

In particular the groups $R_1$, $R_2$, $R_4$, $R_5$, $R_7$ and $R_8$ may have the following meanings:

$R_1$ or $R_2$ (when other than the group $R_4R_5NAlk$): hydrogen or $C_{1-4}$ alkyl (e.g. methyl);

R₄: $C_{1-7}$ alkyl (e.g. methyl, propyl, butyl, isobutyl or heptyl), $C_{1-4}$ alkyl substituted by a trifluoromethyl group (e.g. 2,2,2-trifluoroethyl), $C_{2-4}$ alkyl substituted by a hydroxy or di $C_{1-3}$ alkylamino group (e.g. 3-hydroxypropyl or dimethylaminoethyl), $C_{5-7}$ cycloalkyl (e.g. cyclohexyl), alkenyl (e.g. allyl), phenyl $C_{1-3}$ alkyl (e.g. benzyl), or a heteroaryl $C_{1-3}$ alkyl group where the heteroaryl ring is 5 or 6 membered and contains one heteroatom (e.g. furylmethyl);

R₅: hydrogen or methyl; or

R₄R₅N may represent a 5 to 7 membered ring, optionally containing a double bond or an alkyl (e.g. methyl) group (e.g. piperidino, 4-methylpiperidino, pyrrolidino, hexamethylenimino or tetrahydropyridino);

R₇: hydrogen, methyl, ethyl or 2-hydroxyethyl;

R₈: hydroxy, phenyl $C_{1-3}$ alkyl (e.g. benzyl), $C_{1-4}$ alkyl substituted by hydroxy, $C_{1-3}$ alkoxy, $C_{2-4}$ alkanoyloxy or amino (e.g. hydroxymethyl, 2-hydroxyethyl, acetoxymethyl or aminomethyl); amino, di-$C_{1-4}$ alkylamino (e.g. diethylamino); NHCOR₁₂ where R₁₂ represents hydrogen, $C_{1-3}$ alkyl (e.g. methyl), $C_{1-3}$ alkoxy (e.g. ethoxy), or phenyl; NHCONHR₁₄ where R₁₄ represents phenyl; or N=CHR₁₅ where R₁₅ is phenyl or pyridyl (e.g. 4-pyridyl).

Alk is particularly a methylene or ethylene group, more particularly methylene.

When R₃ is in the 3-position preferably R₂ represents hydrogen.

When R₃ is in the 2-position preferably R₂ represents alkyl (e.g. methyl).

When X is sulphur, n is preferably 1 and m is preferably 2.

Three preferred groups of compounds are as follows:
(i) compounds in which R₃ is in the 3-position and R₁ is the group R₄R₅NAlk, and R₂ is more particularly hydrogen;
(ii) compounds in which R₃ is in the 2-position and R₂ is the group R₄R₅NAlk;
(iii) compounds in which R₃ is in the 2-position and R₁ is the group R₄R₅NAlk, and R₂ is more particularly alkyl (e.g. methyl).

A preferred group of compounds of formula (I) are those in which R₇ is hydrogen or methyl, and R₈ is amino, hydroxyalkyl, alkoxyalkyl, benzyl, formamido, alkanoylamino, aminoalkyl, alkanoyloxyalkyl, hydroxy, aroylamino or phenylcarbamoylamino.

A particularly preferred group of compounds of formula (I) are those of formula (II)

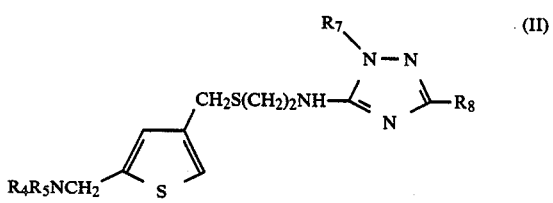

where R₄ and R₅ are methyl groups or together with the nitrogen atom to which they are attached form a pyrrolidino, piperidino or hexamethylenimino group; R₇ is hydrogen or methyl, and R₈ is amino, hydroxyalkyl, alkoxyalkyl, benzyl, formamido, alkanoylamino, aminoalkyl, alkanoyloxyalkyl, hydroxy, aroylamino or phenylcarbamoylamino.

The following compounds and their physiologically acceptable salts are particularly preferred:

1-methyl-N⁵-[2-[[5-[(dimethylamino)methyl-4-methyl-2-thienylmethyl]thio]ethyl]-1H-1,2,4-triazole-3,5-diamine 1-methyl-5-[[2-[[5-(dimethylaminomethyl)-3-thienylmethyl]-thio]ethyl]amino]-1H-1,2,4-triazole-3-methanol 5-[[2-[[[5-(dimethylaminomethyl)-4-methyl]-2-thienylmethyl]-thio]ethyl]amino]-1-methyl-1H-1,2,4-triazole-3-methanol 5-[[2-[[5-(dimethylaminoethyl)-3-thienyl]methyl]thio]ethyl]amino-3-phenylmethyl-1H-1,2,4-triazole.

According to one aspect the invention provides compounds of formula (I) in which one of R₁ and R₂ represents hydrogen and the other represents R₄R₅NAlk and R₃ represents

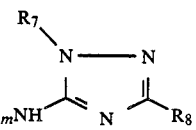

where R₈ represents hydrogen, alkyl, alkenyl, aralkyl, hydroxyalkyl, alkoxyalkyl, hydroxy or alkoxy or R₈ represents the group NR₁₀R₁₁ where R₁₀ represents hydrogen, alkyl, hydroxyalkyl, alkenyl or aralkyl and R₁₁ represents hydrogen, alkyl, hydroxyalkyl, or the group COR₁₂ where R₁₂ represents hydrogen, alkyl, aryl, aralkyl or alkoxy, or R₁₁ represents the group SO₂R₁₃ where R₁₃ represents alkyl or aryl, or R₁₀ and R₁₁ taken together represent the group =CR₁₅R₁₆ where R₁₅ represents aryl and R₁₆ represents hydrogen or alkyl with the proviso that when R₃ is in the 2-position then R₁ represents hydrogen.

According to a further aspect the invention provides compounds of formula (I) in which R₁ is R₄R₅NAlk—, R₂ is halogen or a $C_{1-4}$ alkyl group which may be substituted by hydroxy or $C_{1-4}$ alkoxy and R₃, which is in the 2-position represents

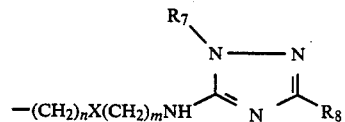

except that R₄ and R₅ do not represent alkynyl or heteroaralkyl and R₄R₅N does not represent a 9 or 10 membered ring.

It will be appreciated in the methods for the preparation of the compounds of formula (I) given below, that for certain reaction steps it may be necessary to protect various reactive substituents in the starting materials for a particular reaction and subsequently to remove the protecting group. Such protection and subsequent deprotection may be particularly pertinent when R₄ and R₅ and/or R₆ are hydrogen, and/or when R₇ is an alkyl group bearing a hydroxy substituent and/or R₈ is an alkyl group bearing a hydroxy or a primary or secondary amino substituent. Standard protection and deprotection procedures can be employed, for example formation of phthalimide, with subsequent cleavage by treatment with a hydrazine e.g. hydrazine hydrate or a primary amine for example methylamine.

In describing the processes which may be used for preparing the compounds of formula (I) or intermediates useful in the preparation thereof, any of $R_1$ to $R_{16}$, Alk, X, E, n and m are as defined in formula (I) unless otherwise stated.

Compounds of formula (I) in which $R_8$ is other than an alkoxy or acyloxyalkyl group or the group $-N=CR_{15}R_{16}$ may be prepared by cyclisation of a compound of formula (III)

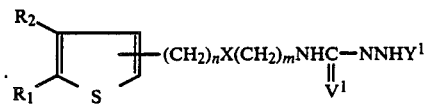

in which $V^1$ is

or NCN and $Y^1$ is hydrogen where V is oxygen or sulphur and $R_8^1$ is a group as defined in formula (I) for $R_8$ or a group convertible thereto under the conditions of the cyclisation reaction or represents halogen or alkoxy; or $V^1$ is NH and $Y^1$ is

In a particular embodiment of the above process compounds of formula (I) in which $R_8$ is amino, hydroxy or a carbon-linked goup may conveniently be prepared by cyclisation of a compound of formula (IV)

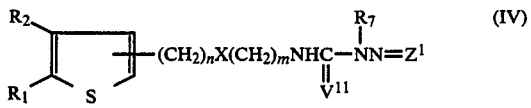

where $V^{11}$ represents the group NCN or

and $Z^1$ represents two hydrogen atoms. The reaction may be carried out in the absence or presence of a suitable solvent, for example, toluene, ethanol, methanol, isopropanol, acetonitrile or water, at a temperature from room temperature to reflux.

It may be convenient to prepare in situ compounds of formula (IV) in which $Z^1$ represents two hydrogen atoms by treating a compound of formula (IV) where $Z^1$ represents a divalent protecting group which can readily be removed to yield two hydrogen atoms, for example a benzylidene group, with an acid, e.g. hydrochloric acid, preferably with heating and under such conditions cyclisation to give compounds of formula (I) will normally occur.

When preparing compounds of formula (I) in which $R_8$ is a hydroxyalkyl group it is preferable that in the intermediate (IV) the hydroxy group is in protected form e.g. as an acyloxy derivative such as an alkanoyloxy or aroyloxy derivative. The protecting group will normally be removed during the cyclisation process.

Intermediates of formulae (III) and (IV) may be prepared from amines of formula (V)

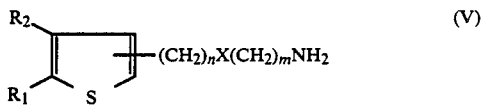

by methods analogous to those described in British patent specification No. 2023133 and European patent specification publication No. 0016565.

Compounds of formula (I) where Alk represents $CH_2$ and in which $R_8$ is other than the group $-N=CR_{15}R_{16}$ may be prepared by reducing the intermediate formed from reacting a compound of formula (VI)

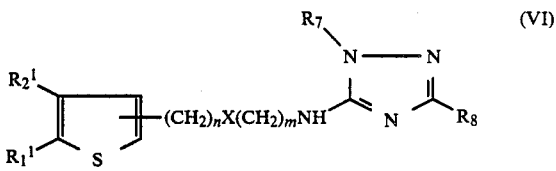

in which one of $R_1^1$ and $R_2^1$ represents hydrogen, halogen or a $C_{1-4}$ alkyl group which may be optionally substituted by hydroxy or $C_{1-4}$ alkoxy and the other represents the group $-CHO$ with a reagent $R_4R_5NH$. Reaction may be effected by treatment with ammonia or an amine $R_4R_5NH$ in a solvent e.g. tetrahydrofuran or an alkanol such as ethanol or methanol, followed by reduction e.g. with a hydride reducing agent such as an alkali metal or alkaline earth metal borohydride, e.g. sodium borohydride, or aluminium hydride or lithium aluminium hydride or with hydrogen and a metal catalyst e.g. palladium or platinum.

Alternatively, for the production of compounds of formula (I) in which $R_8$ is other than $-N=CR_{15}R_{16}$, a compound of formula (I) in which $R_4$ is hydrogen may be reacted with an aldehyde $R_4^1-CHO$ under the reducing conditions described above, the group $R_4^1$ having a meaning such that the resulting group $R_4^1CH_2$ represents a group $R_4$ as defined above. This method applies particularly to the preparation of compounds of formula (I) in which $R_4$ is heteroaralkyl or an optionally substituted alkyl chain containing up to 10 carbon atoms.

In certain instances compounds of formula (I) may be prepared by methods involving interconversion of the substituent $R_8$.

Thus compounds in which $R_8$ is an acyloxyalkyl group may be prepared by treating the corresponding hydroxyalkyl compound with an appropriate acid, e.g. acetic or benzoic acid at elevated temperatures e.g. 80°-120° C. in the absence or presence of a solvent such as toluene.

Compounds of formula (I) in which $R_8$ represents the group $-N=CR_{15}R_{16}$ may be prepared from compounds of formula (I) in which $R_8$ is an $NH_2$ group by reaction with an aldehyde or ketone $R_{15}R_{16}CO$ in a solvent such as benzene, ethanol, or methanol. The reaction is preferably carried out with heating, e.g. at reflux.

Compounds of formula (I) in which $R_8$ is the group $NR_{10}R_{11}$ where $R_{11}$ is $-COR_{12}$, $-SO_2R_{13}$ or $-C(=E)NHR_{14}$ may be prepared by treating a compound of formula (I) in which $R_8$ is the group $-NHR_{10}$ and $R_1$, $R_2$, $R_7$ and $R_{10}$ are as defined in formula (I) or are groups readily convertible thereto with a reagent capable of replacing the hydrogen atom in the group $NHR_{10}$ by the group $R_{11}$ where $R_{11}$ is as defined above.

Thus, for example, reaction with an activated derivative of either a carboxylic acid $R_{12}COOH$ or a sulphonic acid $R_{13}SO_3H$ or reaction with an isocyanate or isothiocyanate $R_{14}NCE$ in which $R_{14}$ has any of the meanings defined for $R_{14}$ in formula (I) except hydrogen or represents an alkali metal atom such as potassium or sodium or an alkoxycarbonyl group, e.g. ethoxycarbonyl, gives a compound of formula (I) in which $R_{11}$ is respectively the group $COR_{12}$, $SO_2R_{13}$ or $C(=E)NHR_{14}$.

Suitable activated derivatives include acid halides e.g. acid chlorides, alkylchloroformates, acid anhydrides including mixed anhydrides (e.g. acetic formic anhydride) or esters such as alkyl esters, orthoesters and (1-alkyl-2-pyridinyl) esters.

The reaction with an acid halide is preferably carried out in the presence of a base e.g. an inorganic base such as sodium hydroxide or an organic base such as triethylamine or pyridine. The reaction with an alkylchloroformate is preferably carried out in the presence of a base, e.g. potassium carbonate or triethylamine, in a solvent such as diemthylformamide. The reaction with an acid anhydride may be carried out in the absence or presence of a solvent such as pyridine.

In the reaction with an isocyanate or isothiocyanate compounds of formula (I) in which $R_{14}$ is other than hydrogen are conveniently prepared by carrying out the reaction in a solvent such as acetonitrile at an elevated temperature, e.g. reflux. Compounds of formula (I) in which $R_{14}$ is hydrogen may be prepared by heating with an appropriate organic isocyanate or isothiocyanate such as ethylcarbonisothiocyanatidate, at an elevated temperature followed by hydrolysis of the resulting ester, for example with a base such as aqueous ethanolic sodium hydroxide.

Compounds of formula (I) may also be prepared by treating a compound of formula (I) in which the group $R_4R_5N$ is replaced by a quaternary ammonium group (e.g. a trimethylammonium group) with an amine $R_4R_5NH$. The reaction may be carried out by heating the quaternary ammonium compound in the amine (e.g. at 100° to 120° C.) or the reaction may be carried out in the presence of a solvent such as an alkanol (e.g. ethanol) at reflux. This process is particularly applicable to compounds in which Alk is $CH_2$.

Amines of formula (V) may be made by a number of methods depending on the precise structure of the compound.

Thus amines of formula (V) in which n is 1 or 2 and X is oxygen or sulphur may be prepared from the corresponding alcohol of formula (VII)

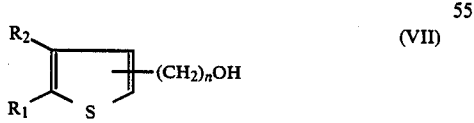

in which n is 1 or 2.

For example amines of formula (V) in which n is 1 and X is sulphur may be prepared by reacting an alcohol of formula (VII) in which n is 1 with an appropriate aminoalkane thiol salt (e.g. cysteamine hydrochloride) in a concentrated mineral acid (e.g. hydrochloric acid).

Amines of formula (V) in which n is 2 and X is sulphur may be prepared by converting an alcohol of formula (VII) in which n is 2 into the corresponding haloalkyl compound using for example thionyl chloride or phosphorus tribromide, or mesylate by reaction with methanesulphonylchloride, followed by treatment with an appropriate aminoalkylthiol (e.g. cysteamine) in a solvent such as ethanol and in the presence of a base (e.g. sodium ethoxide).

Amines of formula (V) in which n is 1 or 2 and X is oxygen may be prepared by treating an alcohol of formula (VII) in which n is 1 or 2 with a suitable base (e.g. potassium t-butoxide) in a solvent (e.g. dimethylformamide) followed by the addition of an appropriate haloalkylamine (e.g. chloropropylamine).

The alcohols of formula (VII), as well as the intermediates (XIX) and (XXI) below, may be made by a variety of processes based on conventional methods in thiophene chemistry (Advances in Heterocyclic Chemistry Volume 1, 1963, page 2–116, Ed. A. R. Katritzky, Academic Press, London and New York; and Comprehensive Chemistry Volume 4, page 787, Ed. P. G. Sammes, Pergamon Press, Oxford). Some representative routes and reagents are given in each case.

Alcohols of formula (VII) in which $R_1$ is the group $R_4R_5NCH_2$, n is 1 and the hydroxymethyl substituent is in either the 2- or 3-position may be prepared by treating a compound of formula (VIII)

with an amine $R_4R_5NH$ under reducing conditions as described previously for the preparation of compounds of the invention, to give a thiophenemethanamine of formula (IX) which may be subsequently reacted with paraformaldehyde in a concentrated mineral acid (e.g. hydrochloric acid) and acetic acid to introduce the hydroxymethyl group at either the 2- or 3-position.

Alcohols of formula (VII) in which $R_2$ is the group $R_4R_5NCH_2$, n is 1 and the hydroxymethyl substituent is at the 2-position may be prepared by reacting a compound of formula (X)

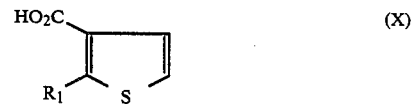

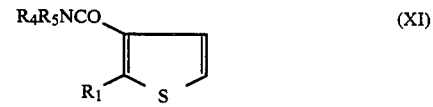

with for example oxalyl chloride in a solvent (e.g. benzene) and preferably in the presence of a catalyst (e.g. pyridine) followed by treatment with an amine $R_4R_5NH$ to give an amide of formula (XI) which is subsequently reduced with a complex metal hydride e.g. lithium aluminium hydride in a solvent such as tetrahydrofuran to give a compound of formula (XII)

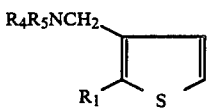 (XII)

The 2-hydroxymethyl group is then introduced by reacting the compound of formula (XII) with formaldehyde or a precursor of formaldehyde such as paraformaldehyde, in a concentrated mineral acid, e.g. hydrochloric acid or acetic acid.

Alcohols of formula (VII) in which $R_1$ is the group $R_4R_5NCH_2$, $R_2$ is hydrogen, n is 1 and the hydroxymethyl substituent is in the 3-position may be prepared from a thiophene 3-carboxylate of formula (XIII)

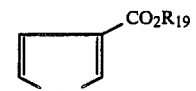 (XIII)

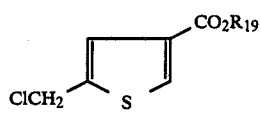 (XIV)

where $R_{19}$ is an alkyl group. This compound is halomethylated e.g. chloromethylated using for example formaldehyde, or a precursor of formaldehyde such as paraformaldehyde, and gaseous hydrogen chloride in a solvent such as chloroform and in the presence of zinc chloride to give a compound of formula (XIV). The amino group $R_4R_5N-$ is then introduced into the compound of formula (XIV) by reaction with an amine $R_4R_5NH$, in a suitable solvent such as ether, to give a compound of formula (XV)

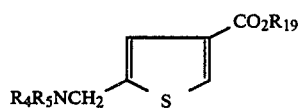 (XV)

Introduction of the 3-hydroxymethyl group is effected by reduction of the 3-carboxylate using for example lithium aluminium hydride in a suitable solvent such as ether.

Alcohols of formula (VII) in which n is 2 may be prepared by lithiating a halothiophene of formula (XVI)

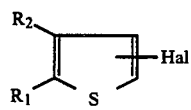 (XVI)

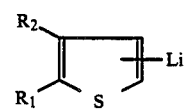 (XVII)

(where Hal is halogen e.g. bromine) using n-butyl lithium in a suitable solvent (e.g. tetrahydrofuran) at a low temperature (e.g. $-78°$), followed by treatment of the resulting lithio derivative (XVII) with ethylene oxide in a solvent such as tetrahydrofuran, to give the desired hydroxyethyl compound (VII, n=2).

In a modification of this process a halothiophene of formula (XVI) in which $R_1$ is a group convertible to $R_4R_5NCH_2-$ (e.g. an aldehyde grouping protected as an acetal) and the group Hal is at the 3-position may be lithiated and treated with ethylene oxide as described above to give a hydroxyethyl compound of formula (XVIII)

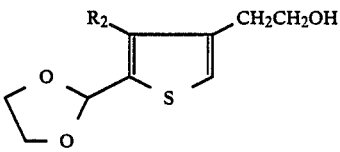 (XVIII)

Subsequent treatment with an amine $R_4R_5NH$ under reducing conditions as described previously for preparing compounds of the invention affords an alcohol of formula (VII) in which $R_1$ is the group $R_4R_5NCH_2$, n is 2 and the hydroxyethyl substituent is at the 3-position.

Amines of formula (V) in which X is $CH_2$ may be prepared from an appropriate haloalkylthiophene of formula (XIX)

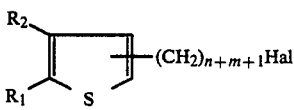 (XIX)

(in which Hal is halogen) by treatment with for example potassium phthalimide in a solvent (e.g. dimethylformamide), followed by deprotection of the phthalimido derivative using for example hydrazine hydrate.

The haloalkylthiophenes of formula (XIX) may be prepared for example by treating a lithio derivative of formula (XVII) with an α,ω-dihaloalkane (e.g. $Br(CH_2)_{n+m+1}Br$) in a solvent such as tetrahydrofuran to give an intermediate of formula (XIX).

Amines of formula (V) in which X is $CH_2$ may also be prepared by methods involving conventional homologation of an alkyl chain. Thus for example a haloalkyl (e.g. chloroethyl) thiophene of formula (XX)

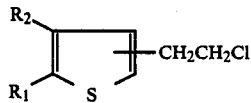 (XX)

may be treated with for example sodium cyanide in dioxan to give the corresponding cyanoethyl compound, which may then be reduced (using for example lithium aluminium hydride in tetrahydrofuran) to give the corresponding aminopropyl compound.

Alternatively a chloroethyl compound of formula (XX) may be treated with malonic ester to give, after decarboxylation, the corresponding butyric acid derivative. This may be treated with thionyl chloride for example, followed by treatment with ammonia, to give the corresponding amide which may then be reduced using for example lithium aluminium hydride to give the corresponding aminobutyl compound.

Amines of formula (V) in which n is zero and X is oxygen may be prepared from an appropriate alkoxythiophene (XXI)

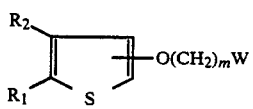

(XXI)

where W is a halogen atom (e.g. chlorine or bromine) or a leaving group (e.g. mesylate), by a similar method to that described above for the preparation of amines of formula (V) in which X is $CH_2$ from the corresponding haloalkyl thiophene.

Alkoxythiophenes of formula (XXI) may be prepared for example by treating a halo (e.g. bromo) thiophene of formula (XVI) with a diol $HO(CH_2)_mOH$ in the presence of a base (e.g. sodium hydride) and cuprous oxide, and preferably with the addition of potassium iodide, to give a hydroxyalkoxy compound of formula (XXII)

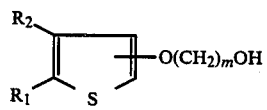

(XXII)

which may be treated with for example, thionyl chloride, phosphorus tribromide or methanesulphonyl chloride to give the alkoxythiophene of formula (XXI).

Amines of formula (V) in which n is zero and X is sulphur may be prepared by treating a lithio derivative of formula (XVII) with elemental sulphur, followed by reaction with an appropriate haloalkylamine (e.g. chloropropylamine) preferably in protected form, e.g. as a phthalimide with subsequent cleavage of the phthalimide group using for example hydrazine hydrate.

Compounds of formula (I) and amines of formula (V) in which Alk is an alkylene group other than $CH_2$ may be prepared from the intermediates described above in which Alk is $CH_2$ or a group convertible thereto (e.g. an ester group) by conventional means for ascending a homologous series. Thus for example a hydroxymethyl group may be converted into a chloromethyl group, which may then be converted into an aminoethyl or aminopropyl group by methods analogous to those described for amines of formula (V) in which X is $CH_2$, and thence into the group $R_4R_5NAlk$ where Alk contains two or three methylene groups.

Intermediates of formula (VI) in which the aldehyde grouping is preferably in protected form (e.g. as an acetal) may be prepared by the methods described above for preparing compounds of the invention except that in the appropriate intermediates the group $R_4R_5NAlk$ is replaced by a protected aldehyde group (e.g. an acetal grouping).

Where the product of any of the above processes is a free base and a salt is required, the salt may be formed in a conventional manner. Thus, for example, a generally convenient method of forming the salts is to mix appropriate quantities of the free base and the acid in an appropriate solvent (s), e.g. an alcohol such as ethanol or an ester such as ethyl acetate.

The invention is illustrated by, but not limited to, the following Examples and Preparations. In the exemplification temperatures are in °C. and t.l.c. refers to thin layer chromatography carried out on silica using one of the following solvent systems unless otherwise stated.

System A: Methanol: 0.88 ammonia (79:1)
System B: Ethyl acetate:isopropanol:water: 0.88 ammonia (25:15:8:2)

PREPARATION 1

(a) Methyl 5-(dimethylaminomethyl)-3-thiophene carboxylate

A solution of methyl 5-(chloromethyl)-3-thiophenecarboxylate (1.9 g) in dry diethylether (100 ml) was treated with anhydrous dimethylamine (5 ml). After 6 hours the solvent was removed in vacuo and the residue was dissolved in 5M hydrochloric acid (20 ml). The aqueous solution was washed with diethylether, basified with 5M sodium hydroxide (30 ml) and extracted with ether. The ethereal extracts were evaporated to give an oily residue which was distilled to yield the title compound as a colourless oil (1.6 g) b.p. 120°–130°/0.5 mm.

The picrate salt was formed in and recrystallised from ethanol m.p. 165°.

The following compounds were similarly prepared from methyl-5-(chloromethyl)-3-thiophenecarboxylate [A] and the corresponding amines:

(b) A (7 g) and pyrrolidine (10 ml) gave methyl 5-(1-pyrrolidinylmethyl)-3-thiophene carboxylate (3.3 g), Picrate salt m.p. 122°–3°

(c) A (6 g) and piperidine (10 ml) gave methyl 5-(1-piperidinylmethyl)-3-thiophenecarboxylate (3.6 g), Picrate salt m.p. 186°.

PREPARATION 2

(a) 5-(Dimethylaminomethyl)-3-thiophenemethanol

A solution of methyl 5-(dimethylaminomethyl)-3-thiophenecarboxylate (1.5 g) in diethylether (50 ml) was treated with lithium aluminium hydride (0.21 g). After 1 hour water (2 ml) was added and the solution was filtered through diatomaceous earth. Evaporation of the filtrate gave an oily residue which distilled to give the title compound as an oil (1.2 g) b.p. (120°/0.1 mm).

The oxalate salt was formed in and recrystallised from ethanol m.p. 107°–8°.

The following compounds were similarly prepared from the corresponding ester.

(b) Methyl 5-(1-pyrrolidinylmethyl)-3-thiophenecarboxylate (3.2 g) gave 5-(1-pyrrolidinylmethyl)-3-thiophenemethanol (2.4 g) Oxalate salt m.p. 111°–2°.

(c) Methyl 5-(1-piperidinylmethyl)-3-thiophenecarboxylate (3.6 g) gave 5-(1-piperidinylmethyl)-3-thiophenemethanol (2.9 g). Oxalate salt m.p. 115°–7° C.

PREPARATION 3

Methyl 5-(hydroxymethyl)-3-thiophenecarboxylate

A solution of methyl 5-(chloromethyl)-3-thiophenecarboxylate (1.7 g) in 50% aqueous acetone (60 ml) was treated with silver nitrate (1.52 g). After 2 h the resulting precipitate was filtered and the filtrate was evaporated. The residue was extracted with diethyl ether, and the ethereal extract was washed with water. Evaporation of the solvent gave an oily residue, which was chromatographed on silica with ethyl acetate-light petroleum 60°–80°; (1:1) to give the title compound as an oil (0.3 g) b.p. 110/0.1 mm m.p. 38°–40°.

PREPARATION 4

5-(Hydroxymethyl)-N,N-dimethyl-3-thiophenecarboxamide

A mixture of methyl 5-(hydroxymethyl)-3-thiophenecarboxylate (3 g), sodium methoxide (0.2 g) and excess anhydrous dimethylamine in dry methanol (20 ml) was stirred for 24 h at ambient temperature. The solvent was removed in vacuo, water was added and the product was extracted with ethyl acetate. The organic extract was evaporated to leave an oily residue which was chromatographed on silica with ethyl acetate-light petroleum 40°-60°; (1:1) to give the title compound (1.3 g).

I.R. (CHBr$_3$) OH 3,595 cm$^{-1}$; C=O 1,620 cm$^{-1}$.

PREPARATION 5

4-(Dimethylaminomethyl)-2-thiophenemethanol

A solution of 5-(hydroxymethyl)-N,N-dimethyl-3-thiophenecarboxamide (1.7 g) in dry tetrahydrofuran (150 ml) was treated with a 0.5M solution of aluminium hydride in tetrahydrofuran (26 ml). After 2 h at room temperature, water (5 ml) was cautiously added and the mixture was filtered through diatomaceous earth. The filtrate was evaporated to leave an oily residue, which was dissolved in 2M hydrochloric acid (20 ml). The aqueous solution was washed with diethyl ether, basified with 5M sodium hydroxide and extracted with ethyl acetate.

The organic extract was distilled to give the title compound as an oil (1 g) b.p. 110/0.1 mm I.R. (CHBr$_3$) OH 3585 cm$^{-1}$; Me$_2$NCH$_2$ 2,775 cm$^{-1}$ and 2,820 cm$^{-1}$.

PREPARATION 6

1-(3-Methyl-2-thienylmethyl)piperidine

A mixture of 3-methyl-2-thiophenecarboxaldehyde (20 g), formic acid (6 ml) and N-formyl piperidine (44.4 ml) was heated under reflux for 12 h. Water (50 ml) and 2M hydrochloric acid (30 ml) were added; and the aqueous solution was washed with ether. The solution was basified to pH 10 with 2M sodium hydroxide (30 ml) and extracted with ether. The organic extract ws evaporated to give a brown oil which was distilled to afford the title compound as a colourless oil (11.8 g) b.p. 70°/0.4 mm.

NMR (CDCl$_3$) 2.9, d, (1H); 3.27, d, (1H); 6.48, s, (2H); 7.6, m, (4H); 7.83, s, (3H); ca 8.5, m, (>6H).

PREPARATION 7

5-(Dimethylaminomethyl)-4-methyl-2-thiophenemethanol

A solution of N,N,3-trimethyl-2-thiophenemethanamine (1.5 g) in dry tetrahydrofuran (50 ml) was treated with a solution of n-butyl lithium (1.6M; 7 ml) at room temperature, under nitrogen. After 4 h, gaseous formaldehyde (excess) was added and the mixture was heated at 40° C. for 20 h.

Water (100 ml) and chloroform (100 ml) were added and the organic solution evaporated in vacuo to leave an oily residue which was dissolved in ethanol (50 ml) and treated with sodium borohydride (0.1 g), followed by acetic acid (10 ml). The reaction mixture was evaporated to dryness and the residue was dissolved in sodium carbonate solution (8%, 50 ml) and extracted with chloroform. The organic extract was distilled to give the title compound as a colourless oil (0.65 g) b.p. 120°/0.1 mm.

The oxalate salt was formed in and recrystallised from a mixture of ethanol and ethyl acetate m.p. 116°-7° C.

(b) Similarly, 1-(3-methyl-2-thienylmethyl)piperidine (3 g) gave 4-methyl-5-(1-piperidinylmethyl)-2-thiophenemethanol as an oil (2.4 g) b.p. 120°/0.2 mm.

N.M.R. (CDCl$_3$) 3.32, s, (1H); 5,32, s, (2H); 6.48, s, (2H); 7.38, brs, (1H); 7.50-7.7, m, (4H); 7.89, s, (3H); 8.30-8.80, m, (6H).

PREPARATION 8

(a)

4-[[2-(Amino)ethyl]thio]methyl-N,N-dimethyl-2-thiophenemethanamine

A mixture of 5-(dimethylaminomethyl)-3-thiophenemethanol (1 g) and 2-aminoethanethiol hydrochloride (0.67 g) was stirred in concentrated hydrochloric acid (7 ml) at 0° C. for 2 hours; and then at room temperature for 48 hours. Solid anhydrous sodium carbonate was added and the product was extracted into ethyl acetate.

The organic extract was distilled to give the title compound as a colourless oil (0.75 g) b.p. 130°/0.05 mm. The oxalate salt was formed in ethanol and recrystallised from ethanol and water m.p. 178°-9°.

The following compounds were similarly prepared from 2-aminoethanethiol hydrochloride (A) and the corresponding thiophenemethanol.

(b) A (1.5 g) and 5-(1-pyrrolidinylmethyl)-3-thiophenemethanol (2.4 g) gave 2[[4-(1-pyrrolidinylmethyl)-2-thienylmethyl]thio]ethanamine (1.4 g). Oxalate salt m.p. 162°-4°.

(c) A (1.6 g) and 5-(1-piperidinylmethyl)-3-thiophenemethanol (2.9 g) gave 2-[[4-(1-pyrrolidinylmethyl)-2-thienylmethyl]thio]ethanamine (2.2 g), Oxalate salt m.p. 89°-91°.

(d) A (0.65 g) and 4-(dimethylaminomethyl)-2-thiophenemethanol (0.9 g) gave 5-[[2-aminoethyl]thio]methyl-N,N-dimethyl-3-thiophenemethanamine (0.8 g) b.p. 130°/0.1 mm. Oxalate salt m.p. 151°-2°.

(e) A (0.6 g) and 5-(dimethylaminomethyl)-4-methyl-2-thiophenemethanol (0.6 g) gave 5-[[2-aminoethyl]thio]methyl-N,N,3-trimethyl thiophenemethanamine as a colourless oil (0.69 g) b.p. 150°/0.1 mm. Oxalate salt m.p. 212° dec.

(f) A (1.11 g) and 4-methyl-5-(1-piperidinylmethyl)-thiophene-2-methanol (2.2 g) gave 2-[[4-methyl-5-(1-piperidinylmethyl)-2-thienylmethyl]thio]ethanamine as a yellow viscous oil (1.88 g) b.p. 170°/0.05 mm.

(g) A (1.2 g) and 4-(1-pyrrolidinylmethyl)-2-thiophenemethanol (1.7 g) gave 2[[4-(1-pyrrolidinylmethyl)-2-thienylmethyl]-thio]ethanamine. b.p. 165°/0.02 mm. Oxalate salt m.p. 147°-8°.

(h) A (1.3 g) and 5-methyl-4-(dimethylaminomethyl)-2-thiophenemethanol (2 g) gave 5-[[2-(aminoethyl)]thio]methyl-N,N,2-trimethyl-3-thiophenemethanamine (1.9 g). Oxalate salt m.p. 146°-7°.

PREPARATION 9

4-(1-Pyrrolidinylmethyl)-2-thiophenemethanol 1-(3-Thienylcarbonyl)pyrrolidine A mixture of 3-thiophenecarboxylic acid (15 g) oxalylchloride (15 ml) and pyridine (0.05 ml) in toluene (100 ml) was heated at reflux for 2 hours. The excess reagent was removed in vacuo and the toluene solution was added to a solution of dry pyrrolidine (25 ml) in dry toluene (100 ml). After 2 h the reaction mixture was washed with dilute hydrochloric acid, 8% aqueous sodium carbonate, saturated brine and water. The organic solution was dried and evaporated to give the title compound (1.8 g) as a white crystalline solid m.p. 70°–73°.

1-(3-Thienylmethyl)pyrrolidine

A solution of 1-(3-thienylcarbonyl)pyrrolidine (12 g) in dry diethylether (200 ml) was added to a slurry of lithium aluminium hydride (2.6 g) in dry diethylether (100 ml). The mixture was stirred for 1 hour, and aqueous 5M sodium hydroxide (20 ml) was added. The mixture was filtered and the filtrate was distilled to give the title compound (9.8 g) as a colourless oil b.p. 120/15 mm.

4-(1-Pyrrolidinylmethyl)-2-thiophenemethanol

A solution of paraformaldehyde (1.5 g) in conc. hydrochloric acid (15 ml) and acetic acid (30 ml) was treated with 1-(3-thienylmethyl)pyrrolidine (2.7 g), and the mixture was stirred for 18 hours, at room temperature.

The mixture was poured onto saturated aqueous sodium carbonate and extracted with chloroform. The chloroform solution was extracted with dilute hydrochloric acid. The aqueous extract was basified with anhydrous sodium carbonate and extracted with chloroform. The chloroform extract was dried and evaporated to give an oil which was purified firstly by thin layer chromatography on silica with a mixture of ethyl acetate:ethanol:0.88 ammonia (40:3:2) as eluant, and finally by distillation to give the title compound (0.8 g) as a colourless oil b.p. 140/0.02 mm.

PREPARATION 10

5-(Dimethylaminoethyl)-3-thiophenemethanol Methyl 5-[(dimethylamino)carbonyl]-3-thiophenecarboxylate A mixture of methyl 3-thiophenecarboxylate (2.8 g) and N,N-dimethylcarbonyl chloride (2.0 ml) was treated with stannic chloride for 5 minutes and the mixture was stirred for 20 hours. Chloroform and iced water were added. The organic solution was washed with 8% aqueous sodium carbonate, dried and evaporated to give a viscous oil. This oil was heated at 70° in vacuo and the residue was dissolved in methyl acetate. Petroleum ether was added to give the title compound (1.1 g) as a crystalline solid m.p. 51°–2° C.

5-(Dimethylaminomethyl)-3-thiophenemethanol

A solution of methyl 5-[(dimethylamino)carbonyl]-3-thiophenecarboxylate (0.5 g) in dry diethylether (50 ml) was added to a slurry of lithium aluminium hydride (0.3 g) in dry diethylether (100 ml). The mixture was stirred for 3 hours at room temperature. Water was cautiously added, the mixture was filtered and the filtrate was evaporated to give the title compound (0.4 g) as a colourless oil b.p. 120°/0.1 mm. The oxalate was formed in and recrystallised from ethanol m.p. 107°–8°.

PREPARATION 11

5-Methyl-4-(dimethylaminomethyl)-2-thiophenemethanol N,N,3-trimethyl-3-thiophene carboxamide A mixture of 2-methyl-3-thiophene carboxylic acid (2 g) and oxalyl chloride (2 ml) in dry toluene (20 ml) was heated under reflux and was treated with pyridine (0.05 ml). The reaction mixture was heated at reflux for 1 h, cooled and partially evaporated. The residue was added to a solution of dimethylamine in toluene at 0° to 5° C. After 2 hours water and diethyl ether were added. The organic phase was washed with dilute hydrochloric acid, sodium hydroxide and water, dried and evaporated to an oil which was distilled to give the title compound (1.4 g) as a colourless oil b.p. 100°/0.1 mm.

N,N,2-Trimethyl-3-thiophenemethanamine

A solution of N,N,3-trimethyl-3-thiophene carboxamide (1.3 g) in dry diethylether (50 ml) was added to a slurry of lithium aluminium hydride (0.3 g) in dry diethylether (100 ml) at room temperature. The mixture was stirred for 1 hour and then water was added. The mixture was filtered and the filtrate was evaporated to give the title compound (0.75 g) as a colourless oil. The picrate salt was formed in ethanol m.p. 155°.

5-Methyl-4-(dimethylaminomethyl)-2-thiophenemethanol

A mixture of N,N,2-trimethyl-3-thiophenemethanamine (6.1 g), paraformaldehyde (3.0 g) in conc. hydrochloric acid (20 ml) and acetic acid (45 ml) was stirred at 0° to 5° C. for 1 hour, and at 8° for 72 hours. The mixture was added to an ice-cold, saturated solution of sodium carbonate. Aqueous 5M sodium hydroxide was added and the mixture was stirred for 20 hours. The solution was extracted with chloroform and the organic extract was washed with dilute sodium hydroxide and saturated brine, dried and evaporated to leave an oil. This residue was distilled to give the title compound (6 g) as a pale yellow oil b.p. 120°/0.1 mm. The oxalate salt was formed in ethanol and ethyl acetate m.p. 129°–131° C.

PREPARATION 12

3-[5-(Dimethylaminomethyl)-3-thiophenemethoxy]-propanamine dioxalate salt

To a solution of 5-(dimethylaminomethyl)-thiophene-3-methanol (5.2 g) and potassium tertiary-butoxide (3.4 g) in dry dimethylformamide (100 ml) was added 3-chloropropylamine hydrochloride (7.8 g) in dimethylformamide (10 ml). The mixture was stirred at 20° for 3 h. A further portion of potassium tertiary-butoxide (6.8 g) was added followed by 3-chloropropylamine hydrochloride (7.8 g) in dimethylformamide (10 ml) and the reaction was stirred at 20° for 18 h. The mixture was concentrated in vacuo, tetrahydrofuran (100 ml) was added followed by potassium carbonate and the mixture was filtered. The filtrate was concentrated, and purified by column chromatography on silica using methanol and methanol:ammonia (79:1) to give an oil (2.2 g). Addition of oxalic acid to a solution of oil in ethanol gave the title compound as an off-white solid, m.p. 176°–178° (d).

Analysis Found: C, 43.6; H, 5.8; N, 6.6; $C_{15}H_{24}N_2O_9S$ requires: C, 44.1; H, 5.9; N, 6.9%.

PREPARATION 13

Dimethyldithio-N-phenacylcarbonimidinothioate

A suspension of potassium carbonate (14.1 g) and dimethyl dithiocarbonimidinothioate hydroiodide (10.2 g) in acetone (150 ml) was stirred at 20° during 2 h. Phenylacetyl chloride (6.8 g) was added dropwise and stirring was continued for 17 h at 20°. The mixture was partially evaporated, diluted with water (300 ml) and extracted with ethyl acetate. The combined organic extracts were evaporated to give the title compound as a pale green oil (7.9 g) b.p. 160°–164°/0.06 mm. T.l.c. ethyl acetate $R_f$ 0.8.

PREPARATION 14

4-[3-(Amino)propoxy]-N,N-dimethyl-2-thiophenemethanamine

4-Bromo-N,N-dimethyl-2-thiophenemethanamine

A mixture of 4-bromo-2-thiophenecarboxaldehyde (4.8 g), dry dimethylformamide (4.3 ml) and 98% formic acid (1.4 ml), was heated at 120° for 30 h. The cooled mixture was poured into water (100 ml) and basified with anhydrous sodium carbonate. Diethyl ether (2×100 ml) was added and the ethereal solution was extracted with dilute hydrochloric acid (50 ml). The aqueous solution was basified with anhydrous sodium carbonate and extracted with diethyl ether (200 ml). The ethereal extracts were distilled to give the title compound (2.5 g) as a colourless oil, b.p. 70°/0.01 mm.

3-[5-(Dimethylaminomethyl)-3-thienyloxy]-1-propanol

A mixture of 1,3-propanediol (20 ml) and sodium hydride (1 g) was stirred at 80° for 1 h. Copper (II) oxide (1.3 g), sodium iodide (0.05 g) and 4-bromo-N,N-dimethyl-2-thiophenemethanamine (5 g) were added and heating was continued for 2 days. Dilute hydrochloric acid (60 ml) was added and the aqueous solution was washed with diethyl ether (50 ml), basified with aqueous sodium hydroxide and extracted with chloroform (200 ml). The organic extract was distilled to give the title compound (1.7 g) as an off-white wax. m.p. 32°–4°.

3-[5-(Dimethylaminomethyl)-3-thienyloxy]-1-propanol methanesulphonate hydrochloride A solution of 3-[5-(dimethylaminomethyl)-3-thienyloxy]-1-propanol (0.25 g) and methanesulphonyl chloride (0.1 ml) in dry dichloromethane (10 ml) at 0°–5° was stirred for 1 h. The mixture was poured onto an ice cold 4% aqueous solution of sodium carbonate (50 ml). The solution was extracted with dichloromethane (20 ml). The organic extract was evaporated to give the title compound (0.05 g) as a white solid.

I.R. (Nujol) 2,550; 2,450, 1,350, 1,170 and 1,195 cm$^{-1}$.

N.M.R. (CDCl$_3$) of base: 3.40, brs (1H); 3.82, d, (1H); 5.62, t, (2H); 5.98, t, (2H); 6.50, s, (2H); 7.01, s, (3H); 7.75–7.80, s+m, (8H).

2-[3-[[5-(Dimethylaminomethyl]-3-thienyloxy]propyl]](1H)-isoindole-1,3-(2H) dione A solution of 3-[5-(dimethylaminomethyl)-3-thienyloxy]-1-propanol methanesulphonate hydrochloride (6 g) in dichloromethane (200 ml) was washed with dilute sodium hydroxide (50 ml). The organic solution was dried (Na$_2$SO$_4$), filtered and evaporated leaving an oil. This oil was dissolved in dry dimethylformamide (100 ml), and potassium phthalimide (3.7 g) was added. The mixture was stirred for 72 h. The excess solvent was removed in vacuo and the residue was dissolved in diethylether (1 l) and washed with water (2 l). The ethereal solution was dried (Na$_2$SO$_4$), filtered and evaporated to give the title compound (4.8 g) as an amber oil.

I.R. (CHBr$_3$) 2,780, 2,820, 1,770, 1,710 cm$^{-1}$.

4-[3-(Amino)propoxy]-N,N-dimethyl-2-thiophenemethanamine

A solution of 2-[3-[[5-(dimethylaminomethyl)-3-thienyloxy]propyl]]-(1H)-isoindole-1,3(2H)-dione (4.6 g) was dissolved in a 30% solution of methylamine in ethanol (100 ml). The mixture was stirred at room temperature for 4 h and heated on a steam-bath for 2 h. The solvent was evaporated and the residue was dissolved in dilute hydrochloric acid (20 ml). The aqueous solution was basified with anhydrous sodium carbonate, washed with diethyl ether (150 ml) and extracted with toluene (200 ml). The toluene solution was distilled to give the title compound (1.6 g) as a colourless oil, b.p. 120°/0.06 mm. The oxalate salt was formed in and recrystallised from ethanol and water m.p. 150°–2°.

PREPARATION 15

5-[(3-Aminopropyl)thio]-N,N,3-trimethyl-2-thiophenemethanamine

N-[3-[[5-(Dimethylamino)methyl-4-methyl-2-thienyl]-thio]propyl]-isoindole-1,3-(2H)-dione A solution of N,N,3-trimethyl-2-thiophenemethanamine (6.2 g) in dry tetrahydrofuran (100 ml) was treated with a solution of n-butyl lithium in hexane (1.6M, 27.5 ml) at 0°, under nitrogen. After 1 h, sulphur (1.4 g) was added. After a further 0.5 h a solution of N-(3-bromopropyl)-isoindole-1,3(2H)-dione (11.8 g) in dry tetrahydrofuran (50 ml) was added and the mixture was stirred at room temperature for 18 h. Water (100 ml) was added and the mixture extracted with ether. The organic extract was evaporated to give the title compound as a yellow oil (15.3 g).

I.R. (CHBr$_3$) 2820, 2775, 1700, 1705, 1392 cm$^{-1}$.

5-[(3-Aminopropyl)thio]-N,N,3-trimethyl-2-thiophenemethanamine

N-[3-[[5-(Dimethylamino)methyl-4-methyl-2-thienyl]thio]propyl]isoindole-1,3(2H)-dione (15.2 g) and hydrazine hydrate (8 ml) were stirred at room temperature in tetrahydrofuran (150 ml) for 48 h. The mixture was filtered and the filtrate was distilled to give the title compound as an orange oil (6.9 g) b.p. 160°–170°/0.04 mm.

PREPARATION 16

5-[4-[(3-Hydroxymethyl-1-methyl-1H-1,2,4-triazol-5-yl)amino]butyl]-3-methyl-2-thiophenecarboxaldehyde

2-(3-Methyl-2-thienyl)-1,3-dioxolane

3-Methyl-2-thiophenecarboxaldehyde (12 g), 1,2-ethanediol (20 ml) and a trace of toluene-p-sulphonic acid were heated at reflux in toluene (250 ml) under Dean and Stark conditions for 4 h. The reaction mixture was cooled and washed with 5% aqueous sodium carbonate solution and water. The toluene solution was evaporated to give an oil which was distilled to give the title compound as a pale yellow oil (14.5 g) b.p. 95°/0.1 mm.

2-[5-(4-Bromobutyl)-3-methyl-2-thienyl]-1,3-dioxolane

A solution of 2-(3-methyl-2-thienyl)-1,3-dioxolane (12.3 g) in dry tetrahydrofuran (150 ml) was treated with a solution of n-butyl lithium in hexane (1.6M, 50 ml) at −60°, under nitrogen. After 1 h, 1,4-dibromobutane (17.3 g) was added and the mixture was stirred at −50° for 3 h and at room temperature for 18 h. Water (75 ml) was added and the mixture extracted with ether. The organic extract was distilled to give the title compound as a light brown oil (15.1 g) b.p. 250°/0.15 mm.

N-[[5-(1,3-Dioxolan-2-yl)-4-methyl-2-thienyl]-4-butyl-]isoindole-1,3(2H)-dione 2-[5-(4-Bromobutyl)-3-methyl-2-thienyl]-1,3-dioxolane (13.3 g) and potassium phthalimide (8.9 g) were stirred at 50° in dry dimethylformamide (130 ml) for 4 h and then at room temperature for 18 h. The mixture was poured into water (1500 ml) and extracted with ether. The organic extract was evaporated to give the title compound as a light yellow oil (16.1 g)

I.R. (CHBr$_3$), 1770, 1710, 1395, 1070, 1033, 720 cm$^{-1}$.

4-[5-(1,3-Dioxolan-2-yl)-4-methyl-2-thienyl]-butanamine

N-[[5-(1,3-Dioxolan-2-yl)-4-methyl-2-thienyl]-4-butyl]-isoindole-1,3(2H)-dione (16.1 g) and hydrazine hydrate (8 ml) were stirred at room temperature in tetrahydrofuran (150 ml) for 24 h. The mixture was filtered and the filtrate was distilled to give the title compound as a red-brown oil (5.34 g), b.p. 230°/0.1 mm.

5-[4-[(3-Hydroxymethyl-1-methyl-1H-1,2,4-triazol-5-yl)amino]butyl]-3-methyl-2-thiophenecarboxaldehyde A mixture of 4-[5-(1,3-dioxolan-2-yl)-4-methyl-2-thienyl]-butanamine (2.73 g) and methyl N-[2-(acetoxy)acetyl]-1-methyl-2-(phenylmethylene)-hydrazinecarboximidothioate (3.38 g) was heated to 60° for 2 h. Toluene (20 ml) and 5N hydrochloric acid (12 ml) were added and the mixture stirred at room temperature for 18 h. The mixture was basified to pH 8, washed with toluene, basified to pH 10 and extracted with ethyl acetate. The extract was evaporated to give an oil which was purified by column chromatography on silica using 3:1 ethyl acetate:methanol as eluent to give the title compound as a pale yellow solid (0.6 g) m.p. 118°-121° (softens).

EXAMPLE 1

(a)

N$^5$-[2-[[5-(Dimethylaminomethyl)-3-thienylmethyl]thio]ethyl]-1-methyl-1H-1,2,4-triazole-3,5-diamine A mixture of 4-[[2-(amino)ethyl]thio]methyl-N,N-dimethyl-2-thiophenemethanamine (0.375 g) and methyl N-cyano-1-methyl-2-(phenylmethylene)hydrazinecarboximidothioate (0.35 g) was heated at 60° in vacuo for 1 hour. The resulting oil was dissolved in toluene (30 ml) and 2M hydrochloric acid (2 ml) was added.

After 3 hours at room temperature 8% aqueous sodium bicarbonate (20 ml) was added and the resulting aqueous solution was washed with toluene. The aqueous solution was further basified with 5M sodium hydroxide (30 ml) and the product was extracted with ethyl acetate. The organic solution was evaporated to give the title compound as an amber oil (0.3 g).

NMR (CDCl$_3$) 3.0, s, (1H); 3.1, s, (1H); 5.6, t, (1H); 6.0, brs, (2H); 6.4, s, (2H); 6.5, s, (2H); 6.6, s+q, (5H); 7.4, t, (2H); 7.8, t, (6H).

T.l.c. System A Rf 0.5. The following compounds were similarly prepared from methyl N-cyano-1-methyl-2-(phenylmethylene)hydrazinecarboximidothioate (A) and the appropriate diamine.

(b) A (0.42 g) and 5-[[2-(amino)ethyl]thio]methyl-N,N-dimethyl-3-thiophenemethanamine (0.4 g) gave N$^5$-[2-[[4-(Dimethylaminomethyl)-2-thienylmethyl]thio]ethyl]-1-methyl-1H-1,2,4-triazole-3,5-diamine (0.3 g).

Assay found: C, 45.3; H, 7.1; N, 24.1. C$_{13}$H$_{22}$N$_6$S$_2$H$_2$O requires: C, 45.4; H, 7.0; N, 24.4%.

NMR (CDCl$_3$) 2.98, 2s (2H); 5.4–5.9, br, (3H); 6.13, s, (2H); 6.55, 6.61, 2s+m, (7H); 7.28 b, (2H); 7.7, s, (6H).

(c) A (0.43 g) and 2-[[4-(1-pyrrolidinylmethyl)-2-thienylmethyl]thio]ethanamine (0.45 g) gave N$^5$-[2-[[5-(1-pyrrolidinylmethyl)-5-thienylmethyl]thio]ethyl]-1-methyl-1H-1,2,4-triazole-3,5-diamine as an amber gum (0.4 g).

Assay found: C, 49.79; H, 6.81; N, 22.83. C$_{15}$H$_{24}$N$_6$S$_2$.H$_2$O requires: C, 49.82; H, 6.97; N, 23.24%.

NMR (CDCl$_3$) 3.0–3.1, 2s, (2H); 5.6 brt, (1H); 6.05, br, (2H); 6.23, s, (2H); 6.33, s, (2H); 6.52, s+m, (5H); 7.31, t, (2H); 7.4, m, (4H); 8.25, m, (4H).

(d) A (0.3 g) and 5-[[2-(aminoethyl)thio]methyl]-N,N,3-trimethyl-2-thiophenemethanamine (0.3 g) gave 1-methyl-N$^5$-[2-[[5-[(dimethylamino)methyl]-4-methyl-2-thienylmethyl]thio]ethyl]-1H-1,2,4-triazole-3,5-diamine as an amber gum (0.15 g).

T.l.c. System A Rf 0.5

N.M.R. (CDCl$_3$) 3.4, s, (1H); 5.7–6.1, t+brs+s, (5H); 6.5–6.6, s+s+m, (7H); 7.2 m, (2H); 7.8, s, (6H); 7.9, s, (3H).

EXAMPLE 2

(a)

1-Methyl-5-[[2-[[5-Dimethylaminomethyl)-3-thienylmethyl]thio]ethyl]amino]-1H-1,2,4-triazole-3-methanol dihydrochloride A mixture of 4-[[2-(amino)ethyl]thio]methyl-N,N-dimethyl-2-thiophenemethanamine (0.4 g) and methyl N-[2-(acetoxy)-acetyl]-1-methyl-2-(phenylmethlene)hydrazinecarboximidothioate (0.56 g) was heated at 60° for 1 h. Toluene (25 ml) and dilute hydrochloric acid (3 ml) were added and the mixture was stirred for 3 h at room temperature and then heated for 30 min. on a steam-bath. Anhydrous sodium bicarbonate was added and the mixture was washed with toluene. The aqueous solution was basified with sodium hydroxide and extracted with ethyl acetate. The ethyl acetate extract was dried [Na$_2$SO$_4$], filtered and evaporated to give an oil, which was purified by column chromatography on silica using methanol to give a gum. This gum was dissolved in methyl acetate (10 ml) and treated with 8% ethereal hydrogen chloride (5 ml). The resulting solid was crystallised from ethanol to give the title compound (0.2 g) as white needles m.p. 182°-4° C.

N.M.R. (D$_2$O) 2.50, 2.66, 2xm, (2H); 5.35, s, (2H); 5.50, s, (2H); 6.19, s, (2H); 5.90, s, (2H); 6.19, s, (2H); 6.38–6.42, s+t, (5H); 7.11–7.20, s+t, (8H).

The following compounds were similarly prepared from methyl N-[2-(acetoxy)acetyl]-1-methyl-2-(phenylmethylene)hydrazinecarboximidothioate [B] and the appropriate diamine.

(b) [B] (1.01 g) and 2-[[[5-(dimethylaminomethyl)-4-methyl]2-thienylmethyl]thio]ethanamine (0.8 g) gave 5-[[2-[[[5-(dimethylaminomethyl)-4-methyl-2-thienylmethyl]thio]ethyl]amino]-1-methyl-1H-1,2,4-triazole-3-methanol (0.73 g) as a pale yellow oil.

N.M.R. (CDCl$_3$) 3.36, s, (1H); 5.45, s+t, (3H); 6.18, s, (2H); 6.46, s+m (8H); 7.16, t, (2H); 7.72, s, (6H); 7.88, s, (3H).

The free base was converted to its citrate salt in dry ethyl acetate.

m.p. 45°-50° (softens).

Analysis Found: C, 44.3; H, 6.1; N, 11.5; $C_{15}H_{25}N_5OS_2C_6H_8O_7H_2O$ requires: C, 44.6; H, 6.2; N, 11.4%.

(c) [B] (0.62 g) and 2-[[4-(1-pyrrolindylmethyl]-2-thienylmethyl]thio]ethanamine (0.51 g) gave 1-methyl-5-[[2-[[[4-(1-pyrrolidinylmethyl)]-2-thienylmethyl]thio]ethyl]amino]-1H-1,2,4-triazole-3-methanol (0.24 g) as a pale yellow gum.

Analysis Found: C, 51.9; H, 6.9; N, 18.4; $C_{16}H_{25}N_5OS_2 0.25H_2O$ requires: C, 51.65; H, 6.91; N, 18.83%.

N.M.R. (CDCl$_3$) 3.05, br, s, (2H); 5.30, t, (1H); 5.52, s, (2H); 6.20, s, (2H); 6.55, m, (7H); 7.32, t, (2H); 7.55, m, (4H); 8.30, m, (4H).

(d) [B] (0.70 g) and 2-[[[4-(Dimethylaminomethyl)-5-methyl]-2-thienylmethyl]-thio]ethanamine (0.5 g) gave 1-methyl-5-[[2-[[[4-(dimethylaminomethyl)-5-methyl]-2-thienylmethyl]thio]ethyl]amino]-1H-1,2,4-triazole-3-methanol (0.22 g) as a brown gum.

Analysis Found: C, 50.3; H, 7.1; N, 20.2; $C_{15}H_{25}N_5OS_2$ requires: C, 50.7; H, 7.1; N, 19.7%.

N.M.R. (CDCl$_3$) 3.13, s, (1H); 5.25–5.50, br.t, s, br.s, (4H); 6.23, s, (2H); 6.50–6.72, s, q, s, (7H); 7.30, t, (2H); 7.70–7.78, 2, xs, (9H).

(e) [B] (1.01 g) and 3-[[5-(Dimethylaminomethyl)]-3-thienylmethoxy]propanamine (0.75 g) gave 5-[[3-[[5-(dimethylaminomethyl)]-3-thienylmethoxy]propyl]amino]-1H-1,2,4-triazole-3-methanol (0.4 g) as a pale yellow oil.

T.l.c. System B: Rf 0.54.

Analysis Found: C, 50.4; H, 7.3; N, 19.1; $C_{15}H_{25}N_5O_2S.1H_2O$ requires: C, 50.4; H, 7.6; N, 19.6%.

(f) [B] (492 mg) and 2-[[[5-(1-Piperidinylmethyl)]-3-thienylmethyl]thio]ethanamine (417 mg) gave 1-methyl-5-[[2-[[[5-(1-Piperidinylmethyl)]-3-thienylmethyl]thio]ethyl]amino]-1H-1,2,4-triazole-3-methanol (500 g) as a pale yellow gum.

T.l.c. 1:1 ethyl acetate-methanol, Rf 0.3.

N.M.R. (CDCl$_3$) 3.02, d, (1H); 3.12, d, (1H); 5.46, s, (2H); 5.5, t, (1H); 6.0, br.s. (1H); 6.36, s, (2H); 6.4, s, (2H); 6.5, s, (3H); 6.5 q, (2H); 7.3, t, (2H); 7.6, m, (4H); 8.5, m, (6H).

(g) [B] (0.57 g) and 2-[[4-Methyl-[5-(1-piperidinylmethyl)]-2-thienylmethyl]thio]ethanamine (0.50 g) gave 1-methyl-5-[[2-[[[4-methyl-5-(1-piperidinylmethyl)]-2-thienylmethyl]-thio]ethyl]amino]-1H-1,2,4-triazole-3-methanol (0.12 g) as a cream colored solid, m.p. 55°.

N.M.R. (CDCl$_3$) 3.4 s, (1H), 5.47–5.58, t+s, (3H); 6.2, s, (2H); 6.48–6.8, 2xs, q, br, s, (8H); 7.2, m, (2H); 7.6, m, (4H); 7.9, s, (3H); 8.5, m, (6H).

(h) [B] (0.75 g) and 4-[3-(amino)propoxy]-N,N-dimethyl-2-thiophenemethanamine (0.5 g) gave 5-[3-[[5-[(dimethylamino)methyl]-3-thienyloxy]propyl]amino]-1-methyl-1H-1,2,4-triazole-3-methanol (0.2 g) m.p. 99°–100°.

T.l.c. System B: Rf 0.55.

(i) [B] (0.905 g) and 5-[(3-aminopropyl)thio]-N,N,3-trimethyl-2-thiophenemethanamine (0.72 g) gave 5-[3-[[5-[(dimethylamino)methyl]-4-methyl-2-thienyl]thio]propyl]amino-1-methyl-1H-1,2,4-triazole-3-methanol (0.35 g) as a pale yellow oil.

T.l.c. System B: Rf 0.6.

N.M.R. (CDCl$_3$) 3.18, s, (1H); 5.45, s, (2H); 5.00, s+br. t, (2H); 6.50, s, (3H); 6.52, q, (2H); 6.54, s, (2H); 7.19, t, (2H); 7.75, s, (6H); 7.90, s, (3H); 8.10, m, (2H).

EXAMPLE 3

(a)

5-[[2-[[5-(Dimethylaminomethyl)-3-thienyl]methyl]thio]ethyl]amino-3-phenylmethyl-1H-1,2,4-triazole To dimethyl dithio-N-phenacylcarbonimidinothioate (1.18 g) in tetrahydrofuran (20 ml) was added 4-[[2-(amino)ethyl]thio]methyl-N,N-dimethyl-2-thiophenemethanamine (1.13 g) in tetrahydrofuran (10 ml) and the reaction mixture stirred at 20° for 5 h. Hydrazine hydrate (2.5 g) was added and the mixture was stirred overnight at 20°. 2N Hydrochloric acid (10 ml) was added and after stirring for 3 h at 20°, the acidic layer was basified with potassium carbonate and extracted with ethyl acetate. The ethyl acetate extracts were evaporated and the residual oil purified by column chromatography on silicon using chloroform followed by chloroform:methanol (19:1) to give the title compound (0.2 g) as a white solid, m.p. 113° after recrystallisation from a mixture of ethyl acetate and light petroleum, b.p. 60°–80°.

Analysis Found: C, 58.6; H, 6.5; N, 17.9; $C_{19}N_{25}N_5S_2$ requires: C, 58.9; H, 6.5; N, 18.1%.

(b) Similarly prepared from 5-[[2-(amino)ethyl]thio]-methyl-N,N,3-trimethyl-2-thiophenemethanamine (1.0 g), dimethyl dithio-N-phenacylcarbonimidinothioate (0.98 g) and hydrazine hydrate (2.1 g) was 5-[[2-[[[5-(dimethylaminomethyl)-4-methyl-2-thienyl]methyl]thio]-ethyl]amino]-3-phenylmethyl-1H-1,2,4-triazole (0.2 g) as a white solid, m.p. 116°–117°(d).

Analysis Found: C, 59.7; H, 5.9; N, 17.2; $C_{20}H_{27}N_5S_2$ requires: C, 59.8; H, 6.8; N, 17.4%.

EXAMPLE 4

(a)

N-[5-[[2-[[[5-[(Dimethylamino)methyl]-4-methyl-2-thienyl]methyl]thio]ethyl]amino]-1-methyl-1H-1,2,4-triazol-3-yl]acetamide A solution of $N^5$-[2-[[[5-[(dimethylamino)methyl]-4-methyl]-2-thienyl]methyl]thio]ethyl]-1-methyl-1H-1,2,4-triazole-3,5-diamine (1.56 g) and acetic anhydride (0.52 g) in pyridine (20 ml) was stirred at room temperature for 24 h. The solution was evaporated to dryness in vacuo and the residual yellow gum was dissolved in water (60 ml). The solution was extracted with ethyl acetate, and to the aqueous fraction was added anhydrous sodium carbonate (3 g). The solution was extracted with ethyl acetate (3×50 ml). The organic extracts were evapoarted in vacuo to give the title compound (1.17 g) as a yellow gum.

Analysis Found: C, 50.0; H, 6.9; N, 21.7; S, 16.8; $C_{16}H_{26}N_6OS_2$ requires: C, 50.2; H, 6.9; N, 22.0; S, 16.8%.

N.M.R. (CDCl$_3$) 1.0, br, (1H); 3.4, s, (1H); 5.2, t, (1H); 6.2, s, (2H); 6.5, s, 6.55, s, ca, 6.5, s, (7H); 7.27, t, (2H); 7.75, m, 7.9, s, (12H).

(b) In a similar manner, 5-[2-[[5-[(dimethylamino)methyl]-3-thienylmethyl]thio]ethyl]-1-methyl-1H-1,2,4-triazole-3,5,diamine (1.15 g) and acetic anhydride (0.35 ml) gave N-[5-[[2-[[5-[(dimethylamino)methyl]-3-thienylmethyl]thio]ethyl]amino]-1-methyl-1H-1,2,4-triazole-3-yl]acetamide as a yellow foam (1.1 g).

T.l.c. System A: Rf 0.53.

N.M.R. (CDCl$_3$) 1.6, br, (1H); 2.98, d, (1H); 3.1, d, (1H); 5.47, t, (1H); 6.3, s, (2H); 6.42, s, (2H); 6.47, s, (3H); 6.53, q, (2H); 7.3, t, (2H); 7.7, m, (9H).

EXAMPLE 5

(a)

5-[[2-[[5-[[(2-Furanylmethyl)amino]methyl]-3-thienylmethyl]thio]ethyl]amino]-1-methyl-1H-1,2,4-triazole-3-methanol

4-[[[2-[(3-Hydroxymethyl-1-methyl-1H-1,2,4-triazol-5-yl)amino]ethyl]thio]methyl]-N,N,N-trimethyl-2-thiophenemethanium iodide To a solution of 5-[[2-[[5-(dimethylaminomethyl)-3-thienylmethyl]thio]ethyl]amino]-1-methyl]-1H-1,2,4-triazole-3-methanol (3.72 g) in acetone (50 ml) was added a solution of methyl iodide (1.94 g) in acetone (10 ml). After stirring at room temperature for 3 h, the oil which separated was triturated to give the title compound (4.65 g) m.p. 146°–149°.

5-[[2-[[5-[[(2-Furanylmethyl)amino]methyl]-3-thienylmethyl]thio]ethyl]amino]-1-methyl-1H-1,2,4-triazole-3-methanol A mixture of 4-[[[2-[(3-hydroxymethyl-1-methyl-1H-,1,2,4-triazol-5-yl)amino]ethyl]thio]methyl]-N,N,N-trimethyl-2-thiophenemethanium iodide (1.12 g) and 2-furanmethanamine (2.25 g) was heated at 140°–160° for 2 h. The oily residue was washed with diethyl ether (5×15 ml) and suspended in water (30 ml) containing anhydrous sodium carbonate (2 g). The suspension was extracted with ethyl acetate (3×30 ml), the combined extract dried and evaporated in vacuo. The oily residue was chromatographed (silica/ethyl acetate-methanol, 1:1) to give the title compound (0.27 g) as an oil.

T.l.c. ethyl acetate:methanol, 1:1 Rf 0.65.

N.M.R. (CDCl$_3$) 2.60, m, (1H); 3.00, brs. (1H); 3.09, brs, (1H); 3.70, dd, (1H); 3.80, d, (1H); 5.50, s+t, (3H); 6.13, s, (2H); 6.23, s, (2H); 6.36, s, 6.52, s+q, (7H); 6.83, brs, (2H); 7.31, t, (2H).

(b) Prepared in a similar manner was: 5-[[2-[[5-[[(Phenylmethyl)amino]methyl]-3-thienylmethyl]thio]ethyl]amino]-1-methyl-1H-1,2,4-triazole-3-methanol (0.40 g) as an oil from 4-[[[2-[(3-hydroxymethyl-1-methyl-1H-1,2,4-triazol-5-yl)amino]ethyl]thio]methyl]-N,N,N-trimethyl-2-thiophenemethanium iodide (1.8 g) and benzenemethanamine (1.0 g) at 120° for 4 h followed by evaporation of the mixture with water (3×20 ml) in vacuo and column chromatography (silica; ethyl acetate-methanol, 3:1).

T.l.c. ethyl acetate-methanol, 1:1 Rf 0.55.

N.M.R. (CDCl$_3$) 2.70, m, (5H); 3.03, brs, (1H); 3.13, brs, (1H); 5.49, s, 5.30, t, (3H); 6.10, s, (2H); 6.20, s, (2H); 6.38, s, 6.54, s+q, (7H); 6.90, brs, (2H); 7.32, t, (2H).

(c) Prepared in a similar way was: 5-[[2-[[5-[(Heptylamino)methyl]-3-thienylmethyl]thio]ethyl]amino]-1-methyl-1H-1,2,4-triazole-3-methanol (0.3 g) from 4-[[[2-[(3-hydroxymethyl-1-methyl-1H-1,2,4-triazol-5-yl)amino]ethyl]thio]methyl]-N,N,N,trimethyl-2-thiophenemethanium iodide (1.8 g) and heptanamine (2.15 g) at 120° for 1 h and 140° for 4 h followed by evaporation of the residue with water (4×20 ml) in vacuo and column chromatography on the residue (silica/methanol-acetyl acetate, 3:1 then silica/ethanol).

N.M.R. (CDCl$_3$): 3.03, d, (1H); 3.13, d, (1H); 5.36, t, (1H); 5.5, s, (2H); 6.15, m, (2H); 6.38, s, (2H); 6.53, s, (3H); 6.55, q, (2H); 6.75, s, (br), (2H); 7.3, m, (4H); 8.3–9.0, m, (10H); 9.13, t, (3H).

T.l.c. ethanol: Rf 0.32.

EXAMPLE 6

5-[4-[[5-(Dimethylamino)methyl-4-methyl-2-thienyl]butyl]amino]-1-methyl-1H-1,2,4-triazole-3-methanol A mixture of 5-[4-[(3-hydroxymethyl-1-methyl-1H-1,2,4-triazol-5-yl)amino]butyl]-3-methyl-2-thiophenecarboxaldehyde (0.55 g) and dimethylamine in industrial methylated spirits (33% w/w) 8 ml was heated at 50° for 18 h. The mixture was cooled and sodium borohydride (0.5 g) was added. The mixture was stirred at room temperature for 2 h, acidified with 2N hydrochloric acid and washed with ethyl acetate. The aqueous phase was basified with sodium carbonate solution and extracted with ethyl acetate. The organic extract was evaporated to give an oil which was purified by column chromatography on silica using 2:1 ethyl acetatemethanol as eluent to give the title compound as a light brown oil (0.22 g).

N.M.R. (CDCl$_3$): 3.68, s, (1H); 5.47, s, (2H); 5.90, t, (1H); 6.3, br.s, (1H); 6.5–6.7, m, (7H); 7.25, ,m, (2H); 7.78, s, (6H); 7.90, s, (3H); 8.3, m, (4H).

I.R. (CHBr$_3$): 3585, 3420, 2820, 2770, 1530 cm$^{-1}$.

EXAMPLES OF PHARMACEUTICAL COMPOSITIONS

| TABLETS: | |
|---|---|
| | mg/tablet |
| Active ingredient | 100.00 |
| Microcrystalline Cellulose BPC | 198.50 |
| Magnesium stearate BP | 1.50 |
| Compression weight | 300.00 |

The active ingredient is sieved through a 250 μm sieve, blended with the excipients and compressed using 9.5 mm punches. Tablets of other strengths may be prepared by altering the compression weight and using punches to suit.

The tablets may be film coated with suitable film forming materials, e.g. methyl cellulose or hydroxypropyl methyl cellulose using standard techniques. Alternatively the tablets may be sugar coated.

INJECTION FOR INTRAVENOUS ADMINISTRATION

| | % w/v |
|---|---|
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of the formula (I)

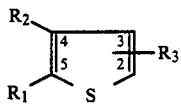

(I)

and physiologically acceptable salts and hydrates thereof, in which one of $R_1$ and $R_2$ represent hydrogen, halogen or a $C_{1-4}$ alkyl group which may be optionally substituted by hydroxy or $C_{1-4}$ alkoxy, and the other represents the group $R_4R_5NAlk$- in which $R_4$ represents hydrogen, $C_{1-10}$ alkyl, $C_{3-8}$ cycloalkyl, $C_{3-6}$ alkenyl, $C_{3-6}$ alkynyl, ar $C_{1-6}$ alkyl, heteroar $C_{1-4}$ alkyl, trifluoro $C_{1-6}$ alkyl, or $C_{1-6}$ alkyl substituted by hydroxy, $C_{1-6}$ alkoxy, amino, $C_{1-6}$ alkylamino, di $C_{1-6}$ alkylamino or $C_{3-8}$ cycloalkyl, and $R_5$ represents hydrogen or a $C_{1-4}$ alkyl group or $R_4$ and $R_5$ may together with the nitrogen atom to which they are attached, form a pyrrolidino, piperidino, hexamethylenimino, heptamethylenimino, tetrahydropyridino, 4-hydroxypiperidino, 4-$C_{1-3}$ alkylpiperidino, morpholino, 2,6-di-$C_{1-3}$ alkylmorpholino or thiamorpholino group;

Alk represents a straight or branched alkylene chain of 1 to 6 carbon atoms;

$R_3$, which may be in either the 2 or 3-position, represents the group

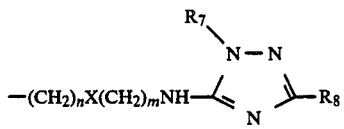

where

X represents —$CH_2$—, —O— or —S—;

n represents zero, 1 or 2 m represents 2, 3 or 4;

$R_7$ represents hydrogen, $C_{1-6}$ alkyl, $C_{3-6}$ alkenyl, ar $C_{1-6}$ alkyl or $C_{2-6}$ alkyl substituted by hydroxy or $C_{1-6}$ alkoxy; and $R_8$ represents hydrogen, $C_{1-6}$ alkyl, $C_{3-6}$ alkenyl, ar $C_{1-6}$ alkyl, hydroxy $C_{1-6}$ alkyl, acyloxy $C_{1-6}$ alkyl, wherein acyl is aroyl or ar $C_{2-7}$ alkanoyl, $C_{1-6}$ alkanoyl, $C_{1-6}$ alkoxy $C_{1-6}$ alkyl, aryloxy $C_{1-6}$ alkyl, ar $C_{1-6}$ alkyloxy $C_{1-6}$ alkyl, amino $C_{1-6}$ alkyl, $C_{1-6}$ alkylamino $C_{1-6}$ alkyl, di $C_{1-6}$ alkylamino $C_{1-6}$ alkyl, hydroxy or $C_{1-6}$ alkoxy, or the group $NR_{10}R_{11}$ where $R_{10}$ represents hydrogen, $C_{1-6}$ alkyl, $C_{1-6}$ alkyl substituted by hydroxy or $C_{1-3}$ alkoxy, $C_{3-6}$ alkenyl, ar $C_{1-6}$ alkyl, heteroar $C_{1-6}$ alkyl, and $R_{11}$ represents any of the groups defined for $R_{10}$ or may represent $COR_{12}$ where $R_{12}$ represents hydrogen, $C_{1-6}$ alkyl, aryl, ar $C_{1-6}$ alkyl, $C_{1-6}$ alkoxy, heteroaryl, heteroar $C_{1-6}$ alkyl or $R_{11}$ represents the group $SO_2R_{13}$ where $R_{13}$ represents $C_{1-6}$ alkyl or aryl or $R_{11}$ represents the group

where E represents oxygen or sulphur, and $R_{14}$ represents hydrogen, $C_{1-6}$ alkyl, $C_{3-8}$ cycloalkyl, aryl or ar $C_{1-6}$ alkyl or $R_{10}$ and $R_{11}$ taken together represent the group =$CR_{15}R_{16}$ where $R_{15}$ represents aryl or heteroaryl and $R_{16}$ represents hydrogen or $C_{1-6}$ alkyl, with the provisos that where $R_2$ represents the group $R_4R_5NAlk$ then $R_3$ is in the 2-position;

where $R_2$ represents hydrogen then $R_3$ is in the 3-position; and where $R_2$ represents halogen or $C_{1-4}$ alkyl optionally substituted by hydroxy or $C_{1-4}$ alkoxy, and $R_3$ is in the 2-position, then $R_8$ cannot represent amino $C_{1-6}$ alkyl, $C_{1-6}$ alkylamino $C_{1-6}$ alkyl, di $C_{1-6}$ alkylamino $C_{1-6}$ alkyl or a group $NR_{10}R_{11}$.

2. A compound according to claim 1, in which the groups $R_1$, $R_2$, $R_4$, $R_5$, $R_7$ and $R_8$ have the following meanings:

$R_1$ or $R_2$ (where other than the group $R_4R_5$ NAlk): a hydrogen or bromine atom or a $C_{1-3}$ alkyl group or a $C_{1-3}$ alkoxy $C_{1-3}$ alkyl group or a hydroxy $C_{1-3}$ alkyl group; or when $R_1$ or $R_2$ is the group $R_4R_5NAlk$, $R_4$: $C_{1-10}$ alkyl, $C_{5-7}$ cycloalkyl, $C_{3-6}$ alkenyl, ar $C_{1-6}$ alkyl, wherein the aryl portion is phenyl or phenyl substituted by one or more $C_{1-3}$ alkyl, $C_{1-3}$ alkoxy or halogen atoms; $C_{1-4}$ alkyl substituted by a trifluoromethyl group, hydroxy $C_{2-4}$ alkyl, $C_{1-3}$ alkoxy $C_{2-4}$ alkyl, di-$C_{1-3}$ alkylamino $C_{1-6}$ alkyl, or heteroaralkyl where the heteroaryl portion represents a furyl, thienyl, pyridyl or thiazolyl ring and the alkylene portion is a methylene, ethylene or propylene grouping; and $R_5$: hydrogen or a methyl or ethyl group; or $R_4R_5N$: pyrrolidino, piperidino, hexamethylenimino, heptamethylenimino, tetrahydropyridino, 4-hydroxypiperidino, 4-$C_{1-3}$ alkylpiperidino, morpholino, 2,6-di-$C_{1-3}$ alkylmorpholino or thiamorpholino group;

$R_7$: hydrogen, $C_{1-4}$ alkyl or hydroxy-$C_{2-4}$ alkyl;

$R_8$: hydrogen, hydroxy, $C_{1-4}$ alkyl, hydroxy $C_{1-4}$ alkyl, $C_{1-3}$ alkoxy $C_{1-4}$ alkyl, phenyl $C_{1-3}$ alkyl, $C_{2-4}$ alkanoyloxy $C_{1-4}$ alkyl, amino $C_{1-4}$ alkyl, amino, $C_{1-4}$ alkylamino, di-$C_{1-4}$ alkylamino, phenyl $C_{1-3}$ alkylamino, or a heteroaryl $C_{1-3}$ alkylamino group; or represents the group $NHCOR_{12}$ where $R_{12}$ represents hydrogen, $C_{1-3}$ alkyl, $C_{1-3}$ alkoxy, furyl, pyridyl, thiazolyl, thienyl, or phenyl optionally substituted by a $C_{1-3}$ alkyl or a $C_{1-3}$ alkoxy group; or represents the group $NHSO_2R_{13}$ where $R_{13}$ represents $C_{1-3}$ alkyl or phenyl optionally substituted by a $C_{1-3}$ alkyl or $C_{1-3}$ alkoxy group; or represents the group $NHCONHR_{14}$ where $R_{14}$ is $C_{1-3}$ alkyl, $C_{5-7}$ cycloalkyl or phenyl optionally substituted by a $C_{1-3}$ alkyl or $C_{1-3}$ alkoxy group, or represents the group $N=CHR_{15}$ where $R_{15}$ is a phenyl or pyridyl group, and Alk is $(CH_2)_p$ where p is 1, 2 or 3.

3. A compound according to claim 1 in which $R_3$ is in the 3- position and $R_1$ is the group $R_4R_5NAlk$.

4. A compound according to claim 1 in which $R_3$ is in the 2-position and $R_1$ is the group $R_4R_5NAlk$.

5. A compound according to claim 1 where Alk is methylene.

6. A compound according to claim 1, in which $R_7$ is hydrogen or methyl and $R_8$ is amino, hydroxy $C_{1-6}$ alkyl, $C_{1-6}$ alkoxy $C_{1-6}$ alkyl, benzyl, formamido, $C_{1-6}$ alkanoylamino, amino $C_{1-6}$ alkyl, $C_{1-6}$ alkanoyloxy $C_{1-6}$ alkyl, hydroxy, aroylamino where the aryl portion is phenyl or phenyl substituted with one or more $C_{1-3}$ alkyl, $C_{1-3}$ alkoxy or halogen atoms; or phenylcarbamoylmino.

7. A compound according to claim 1, corresponding to formula (II),

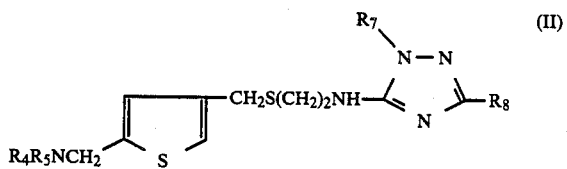

where $R_4$ and $R_5$ are methyl groups or together with the nitrogen atom to which they are attached form a pyrrolidino, piperidino or hexamethylenimino group; $R_7$ is hydrogen or methyl, and $R_8$ is amino, hydroxy $C_{1-6}$ alkyl, $C_{1-6}$ alkoxy $C_{1-6}$ alkyl, benzyl, formamido, $C_{1-6}$ alkanoylamino, amino $C_{1-6}$ alkyl, $C_{1-6}$ alkanoyloxy $C_{1-6}$ alkyl, hydroxy, aroylamino wherein the aryl portion is phenyl or phenyl substituted by one or more $C_{1-3}$ alkyl, $C_{1-3}$ alkoxy or halogen atoms; or phenylcarbamoylamino.

8. A compound according to claim 1 which are:

1-methyl-$N^5$-[2-[[5-[(dimethylamino)methyl]-4-methyl-2-thienylmethyl]thio]ethyl]-1H-1,2,4-triazole-3,5-diamine 1-methyl-5-[[2-[[5-(dimethylaminomethyl)-3-thienylmethyl]thio]ethyl]amino]-1H-1,2,4-triazole-3-methanol 5-[[2-[[[5-(dimethylaminomethyl)-4-methyl]-2-thienylmethyl]-thio]ethyl]amino]-1-methyl-1H-1,2,4-triazole-3-methanol 5-[[2-[[5-(dimethylaminomethyl)-3-thienyl]methyl]-thio]ethyl]amino-3-phenylmethyl-1H-1,2,4-triazole, and their physiologically acceptable salts.

9. A pharmaceutical composition for the treatment of conditions mediated through $H_2$ receptors comprising an effective amount of at least one compound according to claim together with at least one pharmaceutically acceptable carrier or diluent and optionally at least one other active ingredient.

10. A method of treating a condition mediated through histamine $H_2$- receptors which comprises administering to a patient an effective amount of a compound according to claim 1 to relieve said condition.

11. A compound according to claim 6 in which $R_8$ represents amino, hydroxy $C_{1-6}$ alkyl, $C_{1-6}$ alkanoylamino or benzyl.

12. A compound according to claim 1 which is $N^5$-[2-[[5-(Dimethylaminomethyl)-3-thienylmethyl]-thio]ethyl]-1-methyl-1H-1,2,4,-triazole-3,-5-diamine.

* * * * *